United States Patent [19]

Klausener et al.

[11] Patent Number: 4,966,974
[45] Date of Patent: Oct. 30, 1990

[54] 2-PHENYLSULPHINYL-NITRO-PYRIDINES, AND THEIR USE AS FUNGICIDES

[75] Inventors: Alexander Klausener, Stolberg; Wilfried Paulus; Hans-Georg Schmitt, both of Krefeld; Wilhelm Brandes, Leichlingen, all of Fed. Rep. of Germany

[73] Assignee: Bayer Aktiengesellschaft, Leverkusen, Fed. Rep. of Germany

[21] Appl. No.: 332,853

[22] Filed: Apr. 3, 1989

[30] Foreign Application Priority Data

Apr. 13, 1988 [DE] Fed. Rep. of Germany ....... 3812177

[51] Int. Cl.$^5$ ................. C07D 213/61; C07D 213/62; C07D 213/72; A01N 43/40
[52] U.S. Cl. .................................... 546/294; 546/291; 546/295; 546/297
[58] Field of Search ................ 546/294, 291, 295, 297

[56] References Cited

U.S. PATENT DOCUMENTS 4,616,087 10/1986 Wood .................................. 546/294

Primary Examiner—Alan L. Rotman
Attorney, Agent, or Firm—Sprung Horn Kramer & Woods

[57] ABSTRACT

The invention relates to 2-phenylsulphinyl-nitro-pyridines of the formula

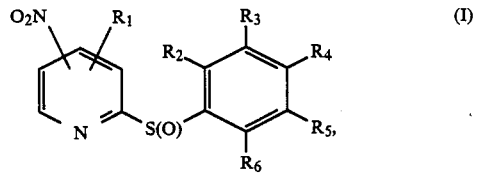

in which
R$_1$ denotes hydrogen, alkyl or halogen and
R$_2$, R$_3$, R$_4$, R$_5$ and R$_6$ independently of one another represent hydrogen, halogen, alkyl, haloalkyl, alkyoxy, haloalkoxy, cyano, nitro, carboxyl, alkoxycarbonyl, carboxamido, N-alkyl- or N,N-dialkylcarboxamido, acyl or primary, secondary or tertiary amino.

processes for their preparation, and their use as microbicides for the protection of materials and fungicides in plant protection.

3 Claims, No Drawings

2-PHENYLSULPHINYL-NITRO-PYRIDINES, AND THEIR USE AS FUNGICIDES

The invention relates to novel derivatives of nitropyridine, processes for their preparation, and their use as microbicides for the protection of materials.

It is already disclosed in U.S. Pat. No. 3,296,272 to use alkylsulphinyl- and alkylsulphonylpolyhalo-pyridines as microbicides for the protection of industrial materials. However, the antimicrobial activity of these alkylsulphinyl- and alkylsulphonyl-pyridines is not satisfactory in certain areas of indication; in particular, they show a disadvantageous sensitivity to hydrolysis when they are used in aqueous systems, for example when they are used as paint fungicides in dispersion paints, in particular when these have an alkaline reaction (for example, see the data in DE-OS (German Published Specification) No. 2,048,354, p. 14).

Surprisingly, it has been found that nitropyridines which are substituted in the 2-position by a phenylsulphinyl group exhibit a considerably improved microbicidal action, a considerably broader range of action and a considerably improved stability to hydrolysis, and are thus much more suitable for use as microbicides in the protection of materials than the halo-pyridines which are substituted by alkylsulphinyl or alkylsulphonyl groups. These nitropyridines which are substituted in the 2-position by a phenylsulphinyl group are novel.

The invention therefore relates to 2-phenylsulphinyl-nitro-pyridines of the formula

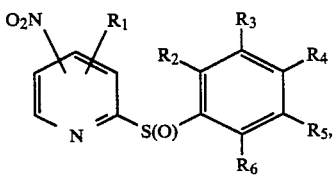

(I)

in which
R$_1$ denotes hydrogen, alkyl or halogen and
R$_2$, R$_3$, R$_4$, R$_5$ and R$_6$ independently of one another represent hydrogen, halogen, alkyl, haloalkyl, alkoxy, haloalkoxy, cyano, nitro, carboxyl, alkoxycarbonyl, carboxamido, N-alkyl- or N,N-dialkylcarboxamido, acyl or primary, secondary or tertiary amino.

Preferred compounds of the formula (I) are those in which
R$_1$ represents hydrogen and
R$_2$, R$_3$, R$_4$, R$_5$ and R$_6$ independently of one another represent hydrogen, halogen, alkyl, haloalkyl, alkoxy, haloalkoxy, cyano or nitro.

Particularly preferred compounds of the formula (I) are those in which the NO$_2$ group is in the 3-, 4- or 5-position, very particularly preferred in the 5-position,
R$_1$ is hydrogen and
R$_2$, R$_5$, R$_6$ independently of one another denote halogen, alkyl, halogenoalkyl or preferably hydrogen and
R$_3$ and R$_4$ independently of one another denote hydrogen, halogen, alkyl or halogenoalkyl.

Examples of representatives which may be mentioned of the 2-arylsulphinylnitropyridines of the formula (I) according to the invention are those in which R$_1$, R$_2$, R$_3$, R$_4$, R$_5$ and R$_6$ have the meaning indicated in Table 1 and the nitro group has the position likewise indicated in Table 1.

TABLE 1

| R$_1$ | NO$_2$ | R$_2$ | R$_3$ | R$_4$ | R$_5$ | R$_6$ |
|---|---|---|---|---|---|---|
| 6-Cl | 3 | H | H | N(CH$_3$)$_2$ | H | H |
| H | 3 | H | OC$_3$H$_7$i | H | H | H |
| H | 3 | H | CN | H | H | H |
| 5-CH$_3$ | 4 | H | H | OCF$_3$ | H | H |
| 6-CH$_3$ | 4 | F | H | Br | H | H |
| 6-C$_3$H$_7$i | 4 | H | Cl | H | H | H |
| 6-Cl | 5 | H | COOCH$_3$ | H | H | H |
| H | 5 | Cl | H | CF$_3$ | H | H |
| H | 5 | H | CH$_3$ | H | H | H |
| H | 5 | H | H | CON(CH$_3$)$_2$ | H | H |
| H | 5 | OCH$_3$ | H | H | H | H |
| H | 5 | Cl | Cl | Cl | Cl | Cl |
| 4-t-C$_4$H$_9$ | 5 | H | CF$_3$ | H | H | Cl |
| H | 5 | H | H | t-C$_4$H$_9$ | H | H |
| H | 5 | H | H | COOC$_4$H$_9$n | H | H |
| H | 5 | H | H | NO$_2$ | H | H |
| H | 6 | H | Cl | H | H | H |
| H | 6 | H | CF$_3$ | H | H | H |
| H | 6 | H | H | COOH | H | H |
| H | 5 | H | H | CF$_3$ | H | H |
| 3-Cl | 5 | H | H | Cl | H | H |

The 2-phenylsulphinyl-nitro pyridines of the formula (I) according to the invention are obtained by oxidizing the corresponding 2-phenylmercapto-nitro-pyridines. The invention therefore also relates to a process for the preparation of the 2-phenylsulphinyl-nitro-pyridines of the formula (I), which is characterized in that 2-phenyl-mercapto-nitro-pyridines of the formula

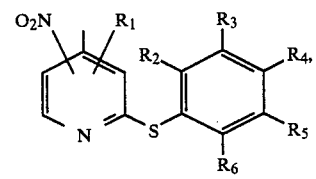

(II)

in which
R$_1$, R$_2$, R$_3$, R$_4$, R$_5$ and R$_6$ have the meaning indicated for formula (I)
are oxidized by processes which are known per se for selectively oxidizing diaryl sulphides or hetaryl-aryl sulphides.

Oxidants which are employed in the process according to the invention are, for example, nitric acid, H$_2$O$_2$ and, preferably, the acyl derivatives of H$_2$O$_2$, the organic per-acids. m-Chloro-peroxybenzoic acid is preferably employed as the oxidant.

The oxidants are employed in an amount such that 0.8 to 1.2 equivalents of per-acid, preferably 1 equivalent of per-acid, is used per equivalent of mercapto compound of the formula (II).

The oxidation is preferably carried out in an organic solvent which is inert under the reaction conditions. Inert solvents which may be mentioned are, above all, halogenated hydrocarbons, such as dichloromethane, trichloromethane, tetrachloromethane, trichloroethane or tetrachloroethane; but aliphatic or aromatic hydrocarbons, such as cyclohexane, benzene, toluene or xylene and also ethers, such as diethyl ether, tetrahydrofuran or dioxane, are also suitable as solvents.

In general, the reaction is carried out under atmospheric pressure, but it can also be effected under reduced or increased pressure.

The oxidation is preferably carried out at temperatures of from −80° to +100° C., preferably at from −20° to +20° C.

The starting compounds of the 2-phenylmercaptonitro-pyridines of the formula (II), which are required for the oxidation, are known or can be obtained following known preparation instructions (see, for example, E. Klingsberg, "Pyridine and Its Derivatives" Part IV Interscience Publishers, J. Wiley & Sons, New York-London-Sydney (1964), R. A. Abramovich (Ed.), "Pyridine and Its Derivatives", Supplement Part IV, J. Wiley & Sons, New York-London-Toronto (1975)).

The invention furthermore relates to the use of the 2-phenylsulphinyl-5-nitro-pyridines of the formula (I) as microbicides for the protection of industrial materials.

The industrial materials to be protected according to the invention encompass non-live materials which have been prepared for use in industry. For example, industrial materials which are to be protected by active compounds according to the invention from microbial change or destruction can be glues, sizes, paper and board, textiles, leather, wood, paints and plastic articles, cooling lubricants and other materials which can be infested or decomposed by microorganisms. Parts of production plants, for example cooling-water circuits, whose function may be impaired by the multiplication of microorganisms may also be mentioned within the scope of the materials to be protected. Industrial materials which may be mentioned within the scope of the present invention are preferably glues, sizes, papers and boards, leather, wood, paints, cooling lubricants and heat-transfer liquids.

Microorganisms, capable of a degradation or a change of the industrial materials, which may be mentioned are, for example, bacteria, fungi, yeasts, algae and slime organisms. The active compounds according to the invention preferably act against fungi, in particular moulds, wood permanently discolouring and wood-destroying fungi, and against slime organisms and algae. Microorganisms of the following genera may be mentioned as examples: Alternaria, such as *Alternaria tenuis*, Aspergillus, such as *Aspergillus niger*, Chaetomium, such as *Chaetomium globosum*, Coniophora, such as *Coniophora puteana*, Lentinus, such as *Lentinus tigrinus*, Penicillium, such as *Penicillium glaucum*, Polyporus, such as *Polyporus versicolor*, Aureobasidium, such as *Aureobasidium pullulans*, Sclerophoma, such as *Sclerophoma pityophila*, Trichoderma, such as *Trichoderma viride*, Escherichia, such as *Escherichia coli*, Pseudomonas, such as *Pseudomonas aeruginosa*, Staphylococcus, such as *Staphylococcus aureus*.

Depending on the field of use, the active compounds to be used according to the invention can be converted to the customary formulations, such as solutions, emulsions, suspensions, powders, pastes and granules.

These can be prepared in a manner known per se, for example by mixing the active compounds with an extender consisting of a liquid solvent and/or solid carriers, if appropriate with the use of surface-active agents, such as emulsifiers and/or dispersing agents, it being possible, where appropriate, for organic solvents, such as alcohols, to be used as auxiliaries, for example when water is used as an extender.

Liquid solvents for the active compounds can be for example water, alcohols, such as lower aliphatic alcohols, preferably ethanol or isopropanol, or benzyl alcohol, ketones, such as acetone or methyl ethyl ketone, liquid hydrocarbons, such as petroleum fractions, halogenated hydrocarbons, such as 1,2-dichloroethane.

In general, the microbicidal agents used for the protection of industrial materials contain an amount of 1 to 95% by weight, preferably of 10 to 75% by weight, of the active compounds.

The application concentration of the active compounds to be used according to the invention depends on the species and the occurrence of the microorganisms to be controlled, and also on the composition of the material to be protected. The optimum amount to be employed can be determined by test series. In general, the application concentrations are in the range of 0.001 to 5% by weight, preferably 0.05 to 1.0% by weight, based on the weight of the material to be protected.

The active compounds to be used according to the invention can also be used in a mixture with other known active compounds. The following active compounds may be mentioned as examples: benzyl alcohol mono(poly)hemiformal and other formaldehyde-releasing compounds, benzimidazolylmethylcarbamates, tetramethylthiuramdisulphide, zinc salts of dialkyl dithiocarbamates, 2,4,5,6-tetrachloroisophthalonitrile, thiazolylbenzimidazole, mercaptobenzothiazole, 2-thiocyanatomethylthiobenzothiazole, methylene bisthiocyanate, phenol derivatives, such as 2-phenyl-phenol, (2,2'-dihydroxy-5,5'-dichloro)-diphenylmethane and 3-methyl-4-chloro-phenol, organo-tin compounds, N-trihalogenomethylthio compounds, such as folpet, fluorofolpet and dichlofluanid, azole fungicides, such as triadimefon, triadimenol and bitertanol.

The 2-phenylsulphinyl-nitro-pyridines of the formula I according to the invention are not only distinguished by a broad range of action against microorganisms which attack industrial materials, but furthermore also exhibit a good fungicidal action against Pyricularia oryzae on rice and a good in-vitro action against phytopathogenic fungi. They can thus also be employed with good success in plant protection against these noxious microbes.

EXAMPLE 1

A total of 60.9 g (0.3 mol) of m-chloroperoxybenoic acid (95% strength) is added in portions and with stirring and cooling to the solution of 80 g (0.3 mol) of 5-nitro-2-(4-chlorophenyl)-mercapto-pyridine in 1000 ml of dioxane at 0° C. When the addition is complete, the reaction mixture is allowed to warm to room temperature, it is stirred at this temperature for 12 hours, and 55 g of pulverulent, anhydrous sodium carbonate are subsequently added. The reaction mixture is subsequently stirred for approximately 4 more hours. After the precipitate has been filtered off and washed with dichloromethane, the filtrate and the wash solutions are combined, and concentrated, and the residue is recrystallized from ethanol/diisopropyl ether.

Yield: 56.1 g (=66.1% of theory)

Melting point: 157° to 159° C.

5-Nitro-2-(4-chlorophenyl)-mercapto-pyridine, which was used as starting compound, had been obtained as follows:

150 g of pulverulent, anhydrous potassium carbonate and 76.7 g (0.52 mol) of 4-chlorothiophenol were added to the solution of 79.3 g (0.5 mol) of 2-chloro-5-nitropyridine in 500 ml of dioxane. The stirred reaction mixture was heated to 100° C. under nitrogen, and maintained at this temperature for approximately 6 hours. After cooling, the reaction mixture was diluted with dichloromethane and washed with water. The organic phase was dried using anhydrous sodium sulphate and subsequently concentrated in vacuo. The residue was recrystallized from toluene/n-hexane.

Yield: 111.2 g (83.3% of theory)
Melting point: 133° to 135° C.

The 2-phenylsulphinyl-nitro-pyridines of the formula (I), in which $R_1$, $R_2$, $R_3$, $R_4$, $R_5$ and $R_6$ have the meaning indicated in Table 2 and the nitro group has the position likewise indicated in Table 2, were prepared in the same manner.

TABLE 3

MICs in mg/c for the action of substances according to the invention on fungi

| Test organisms | Compound 1 | Compound 2 | Compound 3 |
|---|---|---|---|
| Alternaria tenuis | 20 | 35 | 75 |
| Aspergillus niger | 50 | 150 | 100 |
| Aureobasidium pullulans | 50 | 50 | 75 |
| Chaetomium globosum | 20 | 30 | 50 |
| Cladosporium cladosporioides | 5 | 35 | 75 |
| Lentinus tigrinus | 2 | 20 | 10 |
| Penicillium glaucum | 50 | 100 | 75 |
| Sclerophoma pityophila | 10 | 5 | 7,5 |

TABLE 2

| Example | $R_1$ | $NO_2$ | $R_2$ | $R_3$ | $R_4$ | $R_5$ | $R_6$ | M.p. (°C.) |
|---|---|---|---|---|---|---|---|---|
| 2 | H | 5-$NO_2$ | H | $CF_3$ | H | H | H | 95–100 |
| 3 | H | 5-$NO_2$ | H | H | H | H | H | 152–5 |
| 4 | H | 5-$NO_2$ | H | H | Br | H | H | 164 |
| 5 | H | 5-$NO_2$ | H | H | $CH_3$ | H | H | 112–3 |
| 6 | H | 5-$NO_2$ | H | H | F | H | H | 144–9 |
| 7 | H | 5-$NO_2$ | H | $CF_3$ | Cl | H | H | 138–40 |
| 8 | H | 5-$NO_2$ | Cl | $CF_3$ | H | H | H | 131–3 |
| 9 | H | 5-$NO_2$ | Cl | $CF_3$ | Cl | H | H | 114–7 |
| 10 | H | 5-$NO_2$ | Cl | H | Cl | $CF_3$ | H | 144–5 |
| 11 | H | 5-$NO_2$ | Cl | H | Cl | Cl | H | 164–5 |
| 12 | H | 5-$NO_2$ | H | Cl | H | H | H | 142–4 |
| 13 | H | 5-$NO_2$ | H | Cl | H | Cl | H | 154–7 |
| 14 | H | 3-$NO_2$ | H | $CF_3$ | H | H | H | 120 |
| 15 | H | 3-$NO_2$ | H | H | H | H | H | 123–6 |
| 16 | H | 3-$NO_2$ | H | H | Br | H | H | 137–41 |
| 17 | H | 3-$NO_2$ | H | H | $CH_3$ | H | H | 140–1 |
| 18 | H | 3-$NO_2$ | H | Cl | H | H | H | 102–5 |
| 19 | H | 4-$NO_2$ | H | H | Cl | H | H | syrup |
| 20 | H | 4-$NO_2$ | H | Cl | H | H | H | 77–78 |
| 21 | H | 4-$NO_2$ | H | $CF_3$ | H | H | H | syrup |

Use Examples

EXAMPLE A

In order to determine the effectivity against fungi, the minimum inhibitory concentrations (MICs) of active compounds according to the invention are determined:

Active compounds according to the invention are added at concentrations from 0.1 mg/l to 5000 mg/l to an agar which is prepared from brewer's wort and peptone. When the agar has solidified, it is contaminated with pure cultures of the test organisms listed in the table. The cultures are stored for 2 weeks at 28° C. and 60 to 70% relative atmospheric humidity, and the MIC is determined. MIC is the lowest concentration of active compound at which no growth whatsoever by the microbe species used takes place; it is indicated in Table 3 below

EXAMPLE B (Action against slime organisms)

Substances according to the invention which are dissolved in a small amount of acetone are applied in Allen's nutrient solution (Arch. Mikrobiol. 17, 34 to 53 (1952)), which contains 0.2 g of ammonium chloride, 4.0 g of sodium nitrate, 1.0 g of dipotassium hydrogen phosphate, 0.2 g of calcium chloride, 2.05 g of magnesium sulphate, 0.02 g of iron chloride and 1 % of caprolactam per 4 liters of sterile water, at concentrations of in each case 0.1 to 100 mg/l. Shortly before, the nutrient solution is infected with slime organisms (about $10^6$ microorganisms/ml), which have been isolated from spinning water circuits used in the production of nylon. After being cultured for 3 weeks at room temperature, nutrient solutions containing the minimum inhibitory concentration (MIC) or higher concentration of active compound are still completely clear, i.e. the copious multiplication of the microbes and slime formation, which is observed after 3 to 4 days in nutrient solutions not containing active compound, does not take place.

TABLE 4

MIC values indicated in mg/l for the action on slime organisms of the substance indicated below

| Acitve compound | MIC in mg/l |
|---|---|
| 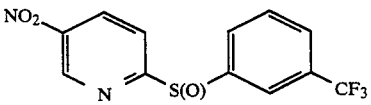 | 15 |

EXAMPLE C

Test of paints for resistance to moulds

Following report 219 of Defense Standards Laboratories Maribyrnong/Australia, the test is carried out as follows:

The paint to be tested is brushed on both sides of a suitable basis.

To obtain results which come close to practice, some of the test pieces are leaded in running water (24 hours;

20° C.) prior to testing for resistance to mould; some others are treated with a stream of warm, fresh air (7 days; 40° C.).

The test pieces thus prepared are placed on an agar nutrient medium. Test piece and nutrient medium are contaminated with fungal spores. Evaluation is carried out after storage of 1 to 3 weeks at 20°±1° C. and 80 to 90% of relative atmospheric humidity. The paint is considered as permanently resistant to moulds when the test piece remains free of fungi or only shows slight infestation at the edges.

Fungal spores of the following nine moulds, which are known for destroying paints or which are frequently found on paints, are used for the contamination:
1. *Alternaria tenuis*
2. *Aspergillus flavus*
3. *Aspergillus niger*
4. *Aspergillus ustus*
5. *Cladosporium herbarum*
6. *Paecilomyces variotii*
7. *Penicillium citrinum*
8. *Aureobasidium pullulans*
9. *Stachybotrys atra Corda*

0 to 1.0% by weight of 2-(3-trifluoromethyl-phenyl)-sulphonyl-5-nitro-pyridine (I), based on the total solids content, was homogeneously incorporated into samples of a commercially available dispersion paint on the basis of polyvinyl acetate.

As a comparison, samples containing 0 to 2% by weight of 4-methylsulphonyl-2,3,5,6-tetrachlorpyridine (II) (commercially available product encompassed by the U.S. Patent Specification) were prepared.

Paints were prepared from the paint samples and tested for resistance to moulds using the method described above.

Result:

Paint samples containing 0.6–1% by weight of (I) produced paints which had an excellent resistance to moulds even under the test conditions described above.

In contrast, no mould-resistant paints were obtained from paint samples containing as much as 2% by weight of (II).

EXAMPLE D

Plasmopara test (vines)/protective

Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous spore suspension of Plasmopara viticola and then remain in a humidity chamber at 20° to 22° C. and 100% relative atmospheric humidity for 1 day. The plants are then placed in a greenhouse at 22° C. and about 80% atmospheric humidity for 5 days. The plants are then moistened and placed in a humidity chamber for 1 day.

Evaluation is carried out 7 days after the inoculation.

In this test, for example the compound of Preparation Example 16 shows a clearly superior activity compared with the prior art.

TABLE 5

| | Plasmopara test (vines)/protective |
|---|---|
| Active compound | Degree of effectiveness as % of the untreated control at an active-compound concentration of 5 ppm |
| 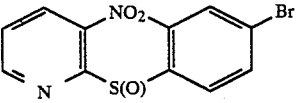 | 92 |

EXAMPLE E

Venturia test (apple)/protective

Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (Venturia inaequalis) and then remain in an incubation cabin at 20° C. and 100% relative atmospheric humidity for 1 day.

The plants are then placed in a greenhouse at 20° C. and a relative atmospheric humidity of about 70%.

Evaluation is carried out 12 days after the inoculation.

In this test, for example the compounds of Preparation Examples 2 and 11 show a clearly superior activity compared with the prior art.

TABLE 6

| | Venturia test (apple)/protective |
|---|---|
| Active compound | Degree of effectiveness as a % of the untreated control at an active-compound concentration of 5 ppm |
| 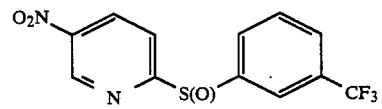 | 87 |

TABLE 6-continued

Venturia test (apple)/protective

| Active compound | Degree of effectiveness as a % of the untreated control at an active-compound concentration of 5 ppm |
|---|---|
| 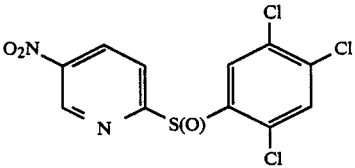 | 83 |
| comparison fungicide of the prior art:<br>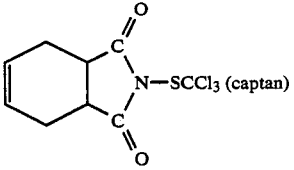 (captan) | 54 |

What is claimed is:

1. A 2-phenylsulphinyl-nitro-pyridine of the formula

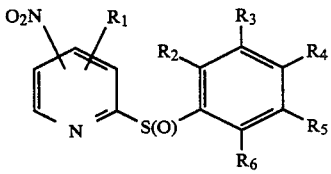

in which
R₁ is hydrogen and
R₂, R₃, R₄, R₅, and R₆ independently of one another are hydrogen, halogen, C₁-C₄-alkyl, trifluoromethyl, C₁-C₃-alkoxy, cyano or nitro.

2. A 2-phenylsulphinyl-nitro-pyridine of claim 1 wherein the nitro group is in the 3-, 4- or 5-position, and R₁ is hydrogen and
R₂, R₃, R₅ and R₆ independently of one another are hydrogen, halogen, C₁-C₄-alkyl or.

3. A 2-phenylsulphinyl-nitro-pyridine of claim 1 wherein the nitro group is in the 5-position and
R₁, R₂, R₅, R₆ are hydrogen and
R₃ and R₄ independently of one another are hydrogen, halogen, C₁-C₄-alkyl or trifluoromethyl.

* * * * *